US009404905B2

United States Patent
Phillips et al.

(10) Patent No.: US 9,404,905 B2
(45) Date of Patent: Aug. 2, 2016

(54) WATER-BASED WETNESS-INDICATING COMPOSITION AND SENSOR

(71) Applicants: Ronnie Lee Phillips, Atlanta, GA (US); Jeffery Richard Seidling, Appleton, WI (US); Corey Thomas Cunningham, Larsen, WI (US); Xuedong Song, Alpharetta, GA (US)

(72) Inventors: Ronnie Lee Phillips, Atlanta, GA (US); Jeffery Richard Seidling, Appleton, WI (US); Corey Thomas Cunningham, Larsen, WI (US); Xuedong Song, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 68 days.

(21) Appl. No.: 13/777,846

(22) Filed: Feb. 26, 2013

(65) Prior Publication Data

US 2014/0241954 A1 Aug. 28, 2014

Related U.S. Application Data

(60) Provisional application No. 61/604,872, filed on Feb. 29, 2012.

(51) Int. Cl.
| | | |
|---|---|---|
| *C09D 5/00* | (2006.01) |
| *G01N 33/18* | (2006.01) |
| *C09D 11/03* | (2014.01) |
| *B05D 1/02* | (2006.01) |
| *B05D 1/18* | (2006.01) |
| *B05D 1/28* | (2006.01) |
| *B05D 3/00* | (2006.01) |
| *C09D 11/037* | (2014.01) |
| *C09D 11/50* | (2014.01) |

(52) U.S. Cl.
CPC ........ *G01N 33/18* (2013.01); *B05D 1/02* (2013.01); *B05D 1/18* (2013.01); *B05D 1/28* (2013.01); *B05D 3/007* (2013.01); *C09D 11/03* (2013.01); *C09D 11/037* (2013.01); *C09D 11/50* (2013.01)

(58) Field of Classification Search
CPC combination set(s) only.
See application file for complete search history.

(56) References Cited

U.S. PATENT DOCUMENTS

| | | | |
|---|---|---|---|
| 4,591,887 A | | 5/1986 | Arbree et al. |
| 5,130,290 A | * | 7/1992 | Tanimoto .................... 503/201 |
| 5,464,470 A | * | 11/1995 | Brachman et al. .......... 106/31.08 |
| 5,883,043 A | | 3/1999 | Halbrook, Jr. et al. |
| 5,888,283 A | | 3/1999 | Mehta et al. |
| 6,124,377 A | | 9/2000 | Kaiser et al. |
| 6,168,655 B1 | | 1/2001 | Nohr et al. |
| 2003/0089270 A1 | | 5/2003 | Shen et al. |
| 2005/0075420 A1 | | 4/2005 | Stovold |
| 2007/0151048 A1 | | 7/2007 | Palacin et al. |
| 2007/0245925 A1 | * | 10/2007 | Li et al. .................... 106/31.17 |
| 2008/0234160 A1 | * | 9/2008 | Wenzel et al. ............... 510/138 |

(Continued)

FOREIGN PATENT DOCUMENTS

| | | |
|---|---|---|
| EP | 1 591 131 A1 | 11/2005 |
| JP | 55-142694 A | 11/1980 |

(Continued)

*Primary Examiner* — Jill Warden
*Assistant Examiner* — Julie Tavares
(74) *Attorney, Agent, or Firm* — Kimberly-Clark Worldwide, Inc.

(57) ABSTRACT

A color-appearing ink composition includes a surfactant blend of at least two non-ionic surfactants having hydrophilic-lipophilic balance values greater than 10, or a non-ionic surfactant having a hydrophilic-lipophilic balance value greater than 10 and a charged surfactant. The composition includes one or more water-insoluble leuco dyes, a developer and a desensitizer. The composition may be applied to a substrate to form a sensor.

6 Claims, 5 Drawing Sheets

(56) References Cited

U.S. PATENT DOCUMENTS

| | | |
|---|---|---|
| 2009/0068633 A1 | 3/2009 | Cohen et al. |
| 2009/0199527 A1 | 8/2009 | Wehr et al. |
| 2010/0030173 A1* | 2/2010 | Song et al. .................... 604/361 |
| 2010/0209839 A1* | 8/2010 | Kabai et al. ................. 430/110.2 |
| 2011/0015599 A1 | 1/2011 | Song et al. |
| 2011/0144603 A1 | 6/2011 | Song |

FOREIGN PATENT DOCUMENTS

| | | |
|---|---|---|
| JP | 3215901 B2 | 10/2001 |
| WO | WO 2007/123966 A1 | 11/2007 |
| WO | WO 2011/073809 A2 | 6/2011 |

* cited by examiner

WATER-BASED WETNESS-INDICATING COMPOSITION AND SENSOR

This application claims priority to Provisional Patent Application No. 61/604,872, filed on Feb. 29, 2012. The entirety of Provisional Patent Application No. 61/604,872 is incorporated herein by reference.

FIELD OF INVENTION

The present invention pertains to a wetness-indicating composition for an aqueous medium. In particular, the present invention describes a water-based medium or ink that can change from being colorless to colored in the presence of an aqueous solution. The ink may be applied to an article such as a substrate to form a sensor.

BACKGROUND

Many products, including consumer, health care, and professional products, are more effectively used by consumers when containing a feature that can communicate or signal to the user that the product is wetted with an aqueous solution (e.g. urine). One example is a visual wetness indicator that causes the product to change color or appearance when wet. Color indicators can either indicate wetness through a change from colorless to colored or vice versa, or through a change in color saturation.

Exemplary consumer products that could be more effective and deliver more benefits to end users by incorporating a suitable color indicator include absorbent articles such as diapers, feminine pads or incontinence pads and garments. Exemplary professional products that could be more effective and deliver more benefits to end users by incorporating a suitable wetness indicator include products for medical use such as bed pads or bandages. Other products that can benefit from a water-based color indicator include wipes, towels and tissues.

Wetness-indicating inks for such products are well known. Desirable performance attributes include durability and non-leachable. These inks, while wettable, are water insoluble.

To date, water-insoluble indicator inks are volatile organic solvent-based inks that contain water-insoluble dye components (e.g. actives). However, the use of volatile organic solvents not only hinders the manufacture of the absorbent articles noted above due to incompatibility with the manufacturing process of cellulose-based products, such use is also not environmentally friendly and more costly.

While the color-changing compositions known in the art prevent leaching in aqueous environments, there remains a need for a water-based wetness-indicating ink that is environmentally friendly and does not leach. Further sought is an ink that is printable at room temperature and provides a readily discernible color change to the un-aided eye. Desirably, the ink is applicable to various articles including substrates used to make the absorbent articles mentioned herein.

SUMMARY OF THE INVENTION

Disclosed is a water-based wetness-indicating ink that includes leuco dyes that are colorless in the presence of a desensitizer. The ink may be printed and dried onto various articles or substrates used to make various articles. When the dried ink contacts water, the desensitizer is dissolved, allowing the leuco dye to interact with a developer to produce a color.

In one aspect of the disclosure is a method for preparing a substrate, the method having the steps of preparing a surfactant blend comprising at least two surfactants having different hydrophilic lipophilic balance profiles; preparing a solubilized active by solubilizing a water-insoluble leuco dye with the surfactant blend and a developer; combining the solubilized active with a binder, a stabilizer and water to create a colored solution; applying the colored solution to the substrate; and drying the substrate so that the applied colored solution becomes colorless.

In another aspect of the disclosure is a color-appearing ink composition including a surfactant blend having at least two non-ionic surfactants having hydrophilic-lipophilic balance values greater than 10. The composition further includes a water-insoluble leuco dye, a developer, a desensitizer, a binder, a stabilizer, and water. In a further aspect, the composition may be applied to a substrate to create a sensor.

In another aspect of the disclosure is a color-appearing ink composition having a surfactant blend including a non-ionic surfactant having a hydrophilic-lipophilic balance value greater than 10, and a charged surfactant. The surfactant may be anionic, amphoteric or zwitterionic. Further included is a water-insoluble leuco dye, a developer, a desensitizer, a binder, a stabilizer, and water. In a further aspect, the composition may be applied to a substrate to create a sensor.

Additional features and advantages of the water-based wetness-indicating ink will be described in the following detailed description. It is understood that the foregoing general description and the following detailed description and examples are merely representative of the invention, and are intended to provide an overview for understanding the invention as claimed.

DETAILED DESCRIPTION

The present invention relates in part to a water-based wetness-indicating ink composition that includes multiple components. The ink is effective even when employing only a single dye. The ink may be applied to a substrate or other object by means of conventional printing techniques. Other application techniques include spraying, painting or dipping. In one aspect, the ink includes a color-developing composition that can change from a largely colorless or pale appearance to a visually distinct or vibrant color when the film layer is exposed to a change in its immediate physical or chemical environment as a result of the introduction of an aqueous medium or mixture.

Figure 1:
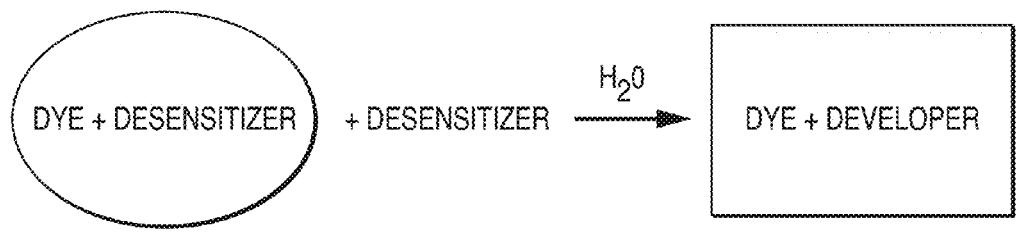
FIG. 1. Shown is a schematic of how the water-based functional ink of the present invention develops color in the presence of water.

Referring to FIG. 1, the water-based indicating ink includes leuco dyes that are colorless in the presence of a desensitizer. When the ink, in a dry state, contacts water, the desensitizer dissolves allowing the leuco dye to interact with a developer. This interaction produces a color.

Mixtures of at least two surfactants with varying hydrophilic-lipophilic balance values are used to solubilize the active water-insoluble dye components. This is the basis of the ink and is referred to as the color-developing composition. Other water-soluble additives may be combined with the color-developing composition to create the ink formulation of the present invention. These additives include an ink binder, a desensitizer, a developer, an ink stabilizer and free water.

Section I—Color-Developing Composition

The present invention involves a color-developing composition that contains at least three major components: (1) a leuco dye, (2) a developer and (3) two surfactants each having a different hydrophilic-lipophilic balance. In addition to these main three components, the color-developing composition may also contain other additives to adjust the physical properties thereof.

Leuco dyes are generally referred to as colorless or pale-colored basic dyes, because the dye molecules can acquire two forms, one of which is colorless. Although not intended to be bound by theory, it is believed that the color developer agent functions as a Lewis acid, which withdraws electrons from the leuco dye molecule to generate a conjugated system. Hence, the leuco dye appears to manifest color from an originally colorless state.

The leuco dyes that may be employed can be selected from a variety of dyes including, for example, phthalide leuco dyes, triarylmethane leuco dyes, and fluoran leuco dyes. Specific examples include (1) Triarylmethane-based dyes, e.g. 3,3-bis(p-dimethylaminophenyl)-6-dimethylaminophthalide, 3,3-bis(p-dimethylaminophenyl)phthalide, 3-(p-dimethylaminophenyl)-3-(1,2-dimethylindol-3-yl)phthalide, 3-(p-dimethylaminophenyl)-3-(2-methylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-6-dimethylaminophthalide, 3,3-bis(2-phenylindol-3-yl)-6-dimethylaminophthalide, 3-p-dimethylaminophenyl-3-(1-methylpyrrol-3-yl)-6-dimethylaminophthalide, etc. (2) Diphenylmethane-based dyes, e.g., 4,4'-bisdimethylaminobenzhydryl benzyl ether, N-halophenylleucoauramine, N-2, 4,5-trichlorophenyl-leucoauramine, etc. (3) Lactam-based dyes, e.g., rhodamine-B-anilinolactam, rhodamine-(p-nitroanilino)lactam, rhodamine-(o-chloroanilino)lactam, etc. (4) Fluoran-based dyes, e.g., 3-dimethylamino-7-methoxyfluoran, 3-diethylamino-6-methoxyfluoran, 3-di-ethylamino-7-methoxyfluoran, 3-diethylamino-7-chlorofluoran, 3-diethylamino-6-methyl-7-chlorofluoran, 3-di-ethylamino-6,7-dimethylfluoran, 3-(N-ethyl-p-toluidino)-7-methylfluoran, 3-diethylamino-7-(N-acetyl-N-methylamino)fluoran, fluoran, 3-diethylamino-7-(N-methylamino)fluoran, 3-diethylamino-7-dibenzylaminofluoran, 3-diethylamino-7-(N-methyl-N-benzylamino)fluoran, 3-diethylamino-7-(N-chloroethyl-N-methylamino)fluoran, 3-diethylamino-7-N-diethylaminofluoran, 3-(N-ethyl-p-toluidino)-6-methyl-7-phenylaminofluoran, 3-(N-ethyl-p-toluidino)-6-methyl-7-(p-toluidino) fluoran, 3-diethylamino-6-methyl-7-phenylaminofluoran, 3-dibutylamino-6-methyl-7-phenylaminofluoran, 3-diethylamino-7-(2-carbomethoxyphenylamino) fluoran, 3-(N-cyclohexyl-N-methylamino)-6-methyl-7-phenylaminofluoran, 3-pyrrolidino-6-methyl-7-phenylaminofluoran, 3-piperidino-6-methyl-7-phenylaminofluoran, 3-diethylamino-6-methyl-7-(2,4-dimethylamino)fluoran, 3-diethylamino-7-(o-chlorophenylamino)fluoran, 3-dibutylamino-7-(o-chlorophenylamino)fluoran, 3-pyrrolidino-6-methyl-7-(p-butylphenylamino) fluoran, 3-(N-methyl-N-n-amylamino)-6-methyl-7-phenylaminofluoran, 3-(N-ethyl-N-n-amylamino)-6-methyl-7-phenylaminofluoran, 3-(N-ethyl-N-isoamylamino)-6-methyl-7-phenylaminofuluoran, 3-(N-methyl-N-n-hexylamino)-6-methyl-7-phenylaminofluoran, 3-(N-ethyl-N-n-hexylamino)-6-methyl-7-phenylaminofluoran, 3-(N-ethyl-N-β-ethylhexylamino)-6-methyl-7-phenylaminofluoran, etc. The basic dyes useful in this invention are not limited to those exemplified above.

Suitable surfactants for usage in this invention include charged and uncharged surfactants. The hydrophobic/lipophilic balance ("HLB") value of the surfactant is a factor in the selection of an uncharged surfactant. An HLB less than 10 indicates more hydrophobic properties, and an HLB value greater than 10 indicates more hydrophilic properties. With lower HLB values (i.e. less miscible with water), surfactants are not able to fully dissolve the leuco dyes. As the HLB value increase, the surfactants become more effective at dissolving the leuco dye.

Table 1 provides a non-exhaustive list of various surfactants that may be suitable for the present invention. The listed surfactants are suitable for dissolving formulation components such as the leuco dye.

TABLE 1

Surfactants

| Surfactant Trade Name | INCI Name | HLB value | Vendor |
| --- | --- | --- | --- |
| LUMULSE 40-L | PEG-8 Laurate | 12.8 | Lambent Technologies |
| TRITON X-100 | Octoxynol-9 | 13.5 | Dow Chemical Company |
| TWEEN 80 | Polysorbate 80 | 18.0 | Sigma-Aldrich |
| DOWFAX 2A1 | Disodium Lauryl Phenyl Ether Disulfonate | >20.0 | Dow Chemical Company |

For uncharged surfactants, nonionic surfactants with HLB greater than 10 are advantageous. Non-limiting examples of nonionic surfactants with an HLB greater than 10 are PEG-8 Laurate, Octoxynol-9 and Polysorbate-80.

Charged surfactants include anionic, amphoteric, and zwitterionic surfactants. Charged surfactants do not fit the requirements to calculate an HLB value. Based on performance, they show a solubilization capability exceeding an HLB value of 20. Specific examples of suitable charged surfactants include but are not limited to Disodium Lauryl Phenyl Ether Disulfonate.

Suitable developers generally include bisphenol A, zinc chloride, zinc salicylate, gallate derivatives such as octyl gallate, propyl gallate, and lauryl gallate, and phenol resins. The most desirable gallate developer is octyl gallate due to its ability to yield a quick, vibrant colored response upon insult.

Figure 2:
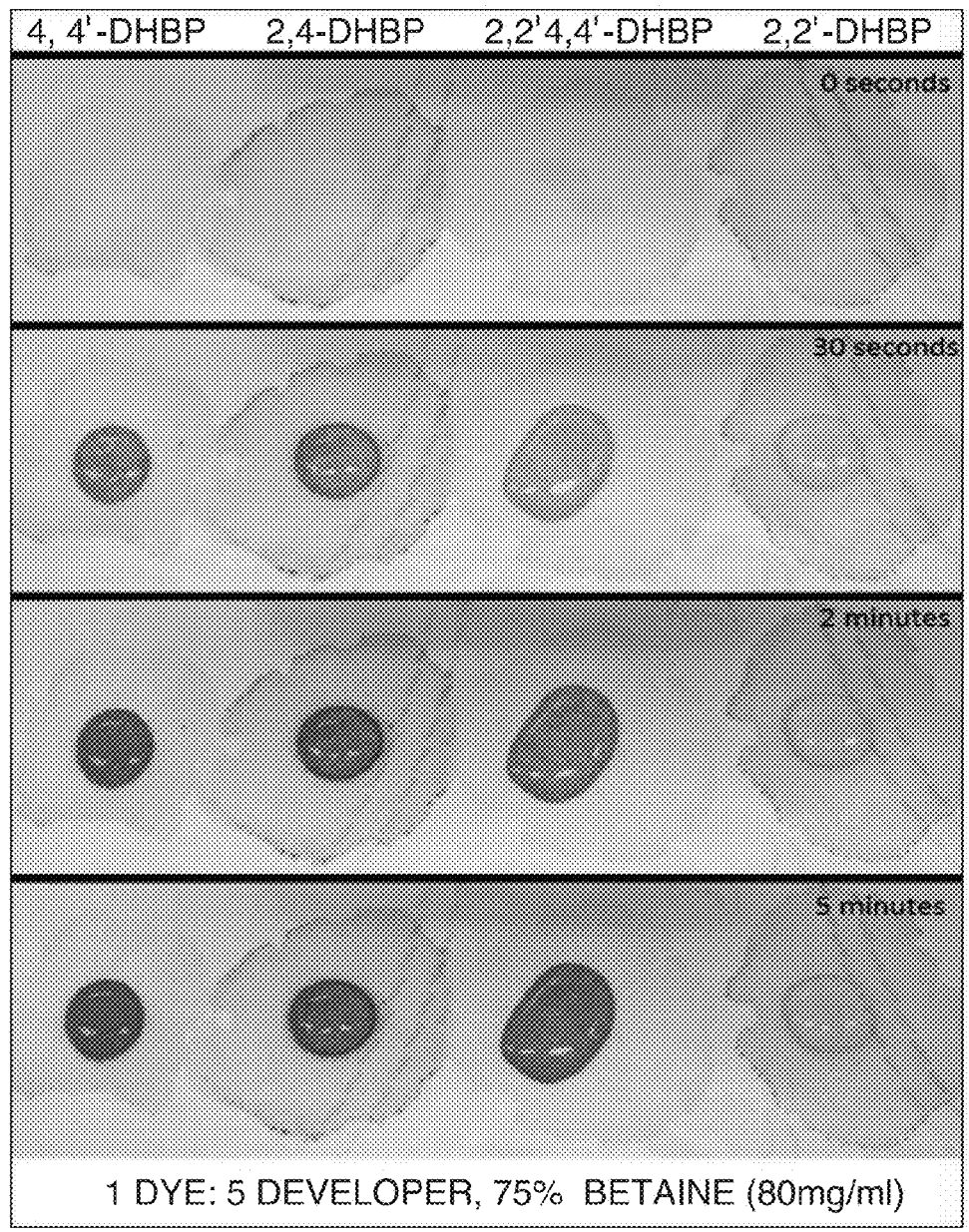
FIG. 2. Shown is polyethylene film treated with several solutions of the present invention, the solutions containing betaine (75 wt. %) 4,4-DHBP (left), 2,4-DHBP (left middle), 2,2'4,4'-DHBP (right middle), and 2,2' DHBP (right), wherein the intensity of each sample was monitored after being wetted with water for 0, 30, 120, and 300 seconds.

Suitable developers further include 2,4-dihydroxybenzophenone; 4,4'-dihydroxybenzophenone; 2,2',4,4'-dihydroxybenzophenone; and 2,2'-dihydroxybenzophenone. Of these developers, the 4,4'-dihydroxybenzophenone ("4,4'-DHBP") is most desirable due to a vibrant color response and absence of yellowing of the substrate to which it may be applied. See FIG. 2.

Other examples of developers that may be used conjointly with the leuco dyes may include: 4-tert-butylphenol, a-naphthol, β-naphthol, 4-acetylphenol, 4-tert-octylphenol, 4,4'-sec-butylidenephenol, 4-phenylphenol, 4,4'-dihydroxydiphenylmethane, 4,4'-isopropylidene diphenol, hydroquinone, 4,4'-cyclohexylidene diphenol, 4,4-dihydroxy diphenylsulfide, 4,4'-thiobis(6-tert-butyl-3-methylphenol), 4,4'-dihydroxydiphenyl sulfone, hydroquinone monobenzyl ether, 4-hydroxybenzophenone, 2,4,4'-trihydroxybenzophenone, 2,2',4,4'-tetrahydroxybenzophenone, dimethyl 4-hydroxyphthalate, methyl 4-hydroxybenzoate, ethyl 4-hydroxybenzoate, propyl 4-hydroxybenzoate, sec-butyl 4-hydroxybenzoate, pentyl 4-hydroxybenzoate, phenyl 4-hydroxybenzoate, benzyl 4-hydroxybenzoate, tolyl 4-hydroxybenzoate, chlorophenyl 4-hydroxybenzoate, phenylpropyl 4-hydroxybenzoate, phenethyl 4-hydroxybenzoate, p-chlorobenzyl 4-hydroxybenzoate, p-methoxybenzyl 4-hydroxybenzoate, novolak type phenol resins, phenol polymers and like phenol compounds.

Section II. Wetness-Indicating Ink

To prepare a color-appearing wetness-indicating ink, the color-developing composition of the present invention is added to a solution containing a desensitizer, a binder, a stabilizer and free water.

Suitable desensitizers are water soluble, of low molecular weight and preferably zwitterionic. Examples of such desensitizers include betaine (trimethylglycine), sodium bis-hydroxyethylglycinate lauryl-glucosides crosspolymer, sodium bis-hydroxyethylglycinate coco-glucosides crosspolymer (available from Colonial Chemical, Inc.), betaine ester-menthol and betaine hydrochloride. Other zwitterionic molecules include 2-(methacryloyloxy)ethyl 3-sulfopropyl ammonium hydroxide and other related ammonium hydroxide derivatives.

Among these desensitizers, betaine derivatives having an average molecular weight of about 100 to about 800 are desirable because the use of such a desensitizer results in excellent decolorization and color formation without tackiness.

The desensitizer is used in an amount effective to inhibit the color forming reaction between the basic dye and the color developing material in the absence of water in the water-sensitive coloring layer. The amount is influenced by factors such as formulation components and amounts thereof, the concentration of the coating composition for forming the water-sensitive coloring layer, the substrate porosity, etc.

Suitable binders are water-based emulsions of water-insoluble polymers binders, cellulose derivatives, polyamides and their copolymers, polyesters and their copolymers, phenolic resins and polyanhydrides. One desirable and commercially available water-soluble binder is AQUAKING Vehicle TV94-5865 (available from Sun Chemical Company).

Stabilizers prevent precipitation of dye components or layer separation within the ink composition. One desirable stabilizer is hydroxypropyl-modified guar gum. Other suitable stabilizers include gum arabic, guar gum, xanthan gum, hydroxyethyl cellulose, methyl cellulose, ethyl cellulose, starches, casein, gelatin, and water-soluble polymers such as polyvinyl alcohol and styrene-maleic anhydride copolymer salt.

The leuco dyes can be present in the composition from about 0.01 wt. % to about 10 wt. %. Typically the amount of leuco dye can be between about 0.05 or 0.1 wt. % to about 4 or 5 wt. %, or 6 or 7 wt. %; desirably the range is between about 0.5 or 1 wt. % to about 2.5, 3 or 5 wt. %, inclusive. The amount of the surfactant blend typically is present from about 1 wt. % to about 15 wt. % or 30 wt. %. Alternatively, the surfactants can be present from about 1, 5, 10 wt. % to about 5, 15, or 30 wt. %, inclusive. The amount of desensitizer typically is present from about 1 wt. % to about 15 wt. % or 30 wt. %. Alternatively, the desensitizer can be present from 1, 10, or 25 wt. % to about 1, 5, or 15 wt. %, inclusive. The amount of developer that is present can range from 1, 10, or 25 wt. % to about 1, 5, or 15 wt. %; typically, between about 1 wt. % to about 25 wt. %. The amount of binder that is present can range from about 10 wt. % or 25 wt. % to about 30 wt. % or 50 wt. %; typically, between about 20 wt. % to about 40 wt. %. The stabilizer is present from about 0.01 wt. % to about 1 wt. %. Typically, the amount of stabilizer is between about 0.1 wt. % to about 0.5 wt. %, inclusive. Finally, the amount of free water typically is present from about 20 wt. % to about 90 wt. %; typically, between about 25, 30, or 35 wt. % to about 80, 85, or 88 wt. %, inclusive.

Section III. Printed Articles

The water-based wetness-indicating ink may be printed or otherwise disposed on various articles or materials. In an aspect of the invention where the ink functions as a color-appearing ink, the formulation, when initially applied to the article, appears colored until air-dried to a colorless or nearly colorless state of appearance (i.e., either no color or very weak background shade). The dried inks show various colors upon being wetted depending on the kind of leuco dye used. Once the indicating ink is printed and dried on the surface of the substrate, the dried solution can manifest color when it contacts a water-containing medium.

In other aspects, a wetness sensor may be composed of a substrate onto which the wetness-indicating ink is deposited. The substrate can be any substrate that allows a deposition of the indicator ink composition to exhibit a color. The substrates may be porous or non-porous. Examples of various substrates include, but are not limited to, porous tissues, papers, polymeric films, metals, wood, plastics, rubbers, woven materials and nonwoven materials that may include a calcium carbonate filler.

"Nonwovens" are materials and webs of material that are formed without the aid of a textile weaving or knitting process. For example, nonwoven materials, fabrics or webs have been formed from many processes such as, for example, meltblowing processes, spunbonding processes, air laying processes, coform processes, and bonded carded web processes.

"Coform" refers to a blend of meltblown fibers and absorbent fibers such as cellulosic fibers that can be formed by air forming a meltblown polymer material while simultaneously blowing air-suspended fibers into the stream of meltblown fibers. The meltblown fibers and absorbent fibers are collected on a forming surface, such as provided by a belt. Two U.S. patents describing coform materials are U.S. Pat. No. 5,100,324 to Anderson et al. and U.S. Pat. No. 5,350,624 to Georger et al., both of which are incorporated in their entirety in a manner consistent herewith.

"Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface or support to form a web of randomly dispersed meltblown fibers. Such a process is disclosed, for example, in U.S. Pat. No. 3,849,241 to Butin et al. which is incorporated in their entirety in a manner consistent herewith.

"Spunbonded fibers" refers to small diameter fibers which are formed by extruding molten thermoplastic material as filaments from a plurality of fine, usually circular capillaries of a spinneret with the diameter of the extruded filaments then being rapidly reduced to fibers as by, for example, in U.S. Pat.

No. 4,340,563 to Appel et al.; U.S. Pat. No. 3,692,618 to Dörschner et al.; U.S. Pat. No. 3,802,817 to Matsuki et al.; U.S. Pat. Nos. 3,338,992 and 3,341,394 to Kinney; U.S. Pat. No. 3,502,763 to Hartman; and U.S. Pat. No. 3,542,615 to Dobo et al., the contents of which are incorporated herein by reference in their entirety in a manner consistent herewith.

In accordance with the present disclosure, one or more sensors described herein can ultimately be integrated into an absorbent article. An "absorbent article" generally refers to any article capable of absorbing water or other fluids. Examples of some absorbent articles include, but are not limited to: personal care absorbent articles, such as diapers, training pants, absorbent underpants, incontinence articles, feminine hygiene products (e.g., sanitary napkins), swim wear, baby wipes, and so forth; and medical absorbent articles, such as garments, fenestration materials, underzones, bed-zones, bandages, absorbent drapes, and medical wipes, food service wipers, clothing articles, and so forth. Materials and processes suitable for forming such absorbent articles are well known to those skilled in the art. Many of the above-noted absorbent articles include a substantially liquid-impermeable layer (e.g., outer cover), a liquid-permeable layer (e.g., bodyside liner, surge layer, etc.), and an absorbent core.

The wetness-indicating ink is applied either at discrete localized spots on the surface of said substrate or generally over the entire substrate or article surface. Alternatively, the indicating ink is applied to same in different patterns and shapes. The substrate or article may have multiple indicating inks applied to different portions thereof.

Section IV. Examples

Water Tolerability:

To determine the miscibility of the surfactants with water, 1 mL of each surfactant of Table 1, (supra) was tested with increasing percentages of water ranging from 30-90% total volume. A 1:5 crystal violet lactone: 4,4'-DHBP powder blend (0.2 g) with betaine (1 mL of 1 g/mL in water) was added to ensure that the formulation components were compatible with the water-based wetness-indicating ink. Upon stirring, the solutions were visually inspected to evaluate such compatibility. PEG-8 Laurate and Polysorbate-80 showed the highest compatibility with components and water respectively. PEG-8 Laurate and Polysorbate-80 were tested in combination. Weight percent ratios of 1:1, 3:1, 5:1 of PEG-8 Laurate and Polysorbate-80 were tested at the aforementioned volume percentages of water. The color response intensity of the inks was reevaluated to determine optimal ratios of ink components. A small amount of the 1:5 crystal violet lactone: 4,4'-DHBP powder blend (0.2 g) was stirred into 1 mL of the surfactant mixtures. Once a strong blue color was seen, 1 mL of the betaine solution (1 g/mL in water) and the appropriate amount of free water were added. The resulting ink was disposed onto cellulosic filter paper and, after drying, appeared colorless. Upon insult with water, a colored response was observed. The strongest color-appearance was observed with formulations using 3:1 and 5:1 PEG-8 Laurate: Polysorbate-80 mixtures. (The 3:1 mixture is hereinafter referred to as the "surfactant mixture").

Addition of Binders:

To determine the binder compatibility with the color-developing composition, seven commercial water-based binders were tested with Green-2 leuco dye. Binders were mixed at 0, 20, 40, and 60 total weight percent with 1 mL (10 wt. %) of the surfactant mixture and appropriate free water.

Figure 3:
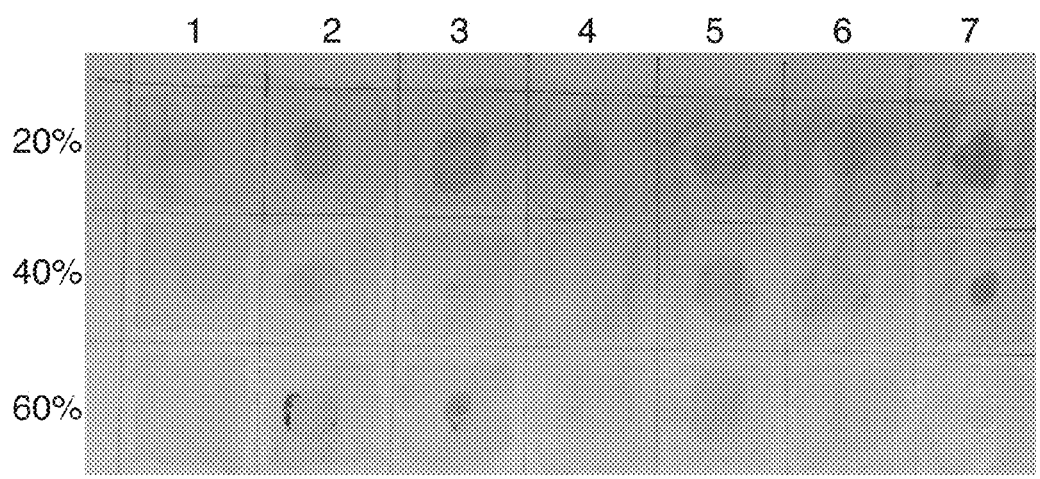
FIG. 3. Shown are seven commercial water-based binders with Green-2 dye at 20, 40 and 60 wt. % binder for each.
Figure 4:
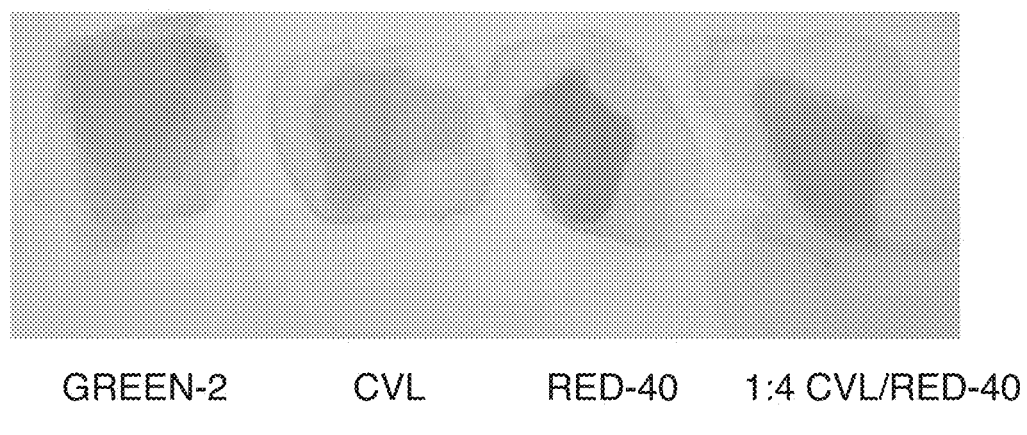
FIG. 4. Shown are four leuco dyes, Green-2, CVL, Red-40 and 1:4 CVL/Red-40 blend, combined with 40 wt. % AQUAKING varnish.

As seen in FIG. 3, some of the binders assisted in color intensity enhancement, while others did not allow any color development at all. The binder which yielded the most vibrant color response (Binder 7: AQUAKING Vehicle TV94-5865; 40 wt. % ("AQUAKING varnish")) was further evaluated with additional leuco dyes as seen in Table 2 (Green-2, CVL, Red-40, and CVL/Red-40 blend) to determine the functionality of each color-developing composition with a selected binder. The dye:developer volume ratios differed for each dye as indicated in Table 3. The AQUAKING binder was compatible with all tested formulations as seen in FIG. 4.

TABLE 2

|  | Green-2 | CVL | Red-40 | Purple |
|---|---|---|---|---|
| Volume Ratio of Dye:Developer | 1:6 | 1:5 | 1:8 | 1:6 (dye-1:4 CVL:Red-40) |
| Desensitizer: All contain water (4.3 g) and varnish (4.0 g) | 600 µL betaine solution | 700 µL betaine solution | 1200 µL betaine solution | 800 µL betaine solution |

Stabilizers:

Stabilizers prevent precipitation of formulation components or layer separation within the formulation. Stabilizers were tested in varying weight percentages of the total formulation weight. These formulations contain wetness-indicating ink components: dye (Green-2), developer 11 (4,4'-DHBP), desensitizer (betaine), binder (AQUAKING varnish), free water and the stabilizers below. Guar and xanthan gums were tested at 0.20, 0.35, and 0.42 wt. % by making 10.0 mg/mL stock solutions of the individual gums and adding 2.0, 3.5, and 4.2 mL respectively. Hydroxyethylcellulose (HEC) was tested at 0.35, 0.55, and 0.75 wt. % by making 20 mg/mL and 40 mg/mL stock solutions and adding 1.75, 2.75, and 3.75 mL respectively. Hydroxypropyl-modified guar gums, JAGUAR HP 8 FF, JAGUAR HP 60, JAGUAR HP 105, and JAGUAR HP 418, were tested at 0.20, 0.35, 0.45, 0.50, 0.60, and 0.70 wt. % with 10 mg/mL and 15 mg/mL stock solutions. Vials of the wetness-indicating ink were allowed to sit for 24 hours to monitor settling. While the formulation with hydroxypropyl-modified guar gum JAGUAR HP 60 (0.70 wt. %) exhibited the best stability and color development upon insult with water, it did not completely remedy the layer separation and/or precipitation of formulation components. Other methods of solubilization may be desired in place of or in addition to the stabilizer.

Micelle Formation with Sonication: Without being bound by theory, it is thought that ultrasonic bombardment assists in the formation of small micelles. Therefore, sonication experiments were performed to see if solutions may be stabilized with a sonification process.

First, four sets of solutions were prepared, three solutions per set. All twelve solutions 1(A, A2 and B, B2), 2(A, A2 and B, B2) and 3(A, A2 and B, B2) consisted of the following: Green-2 dye (30 mg), 4,4'-DHBP (180 mg), 3:1 surfactant mixture (1.5 g), water (2.0 g), Jaguar HP 60 stabilizer (4 mL of 15 mg/mL), and Aquaking binder (2.5 g). Solutions 2(A, A2 and B, B2) and 3(A, A2 and B, B2) were the same as solution 1(A, A2 and B, B2) but with double and triple the amount of surfactant respectively. Further, betaine solution (1.5 mL of 1 g/mL) was added to solutions 1(A2 and B2), 2(A2 and B2) and 3(A2 and B2).

Each solution pair was stirred on a hot plate. Solutions 1 B,B2; 2 B,B2; and 3 B,B2; were subjected to one minute of sonication at 20 mHz using a MISONIX™ MICROSON XL sonicating tip.

Figure 5:
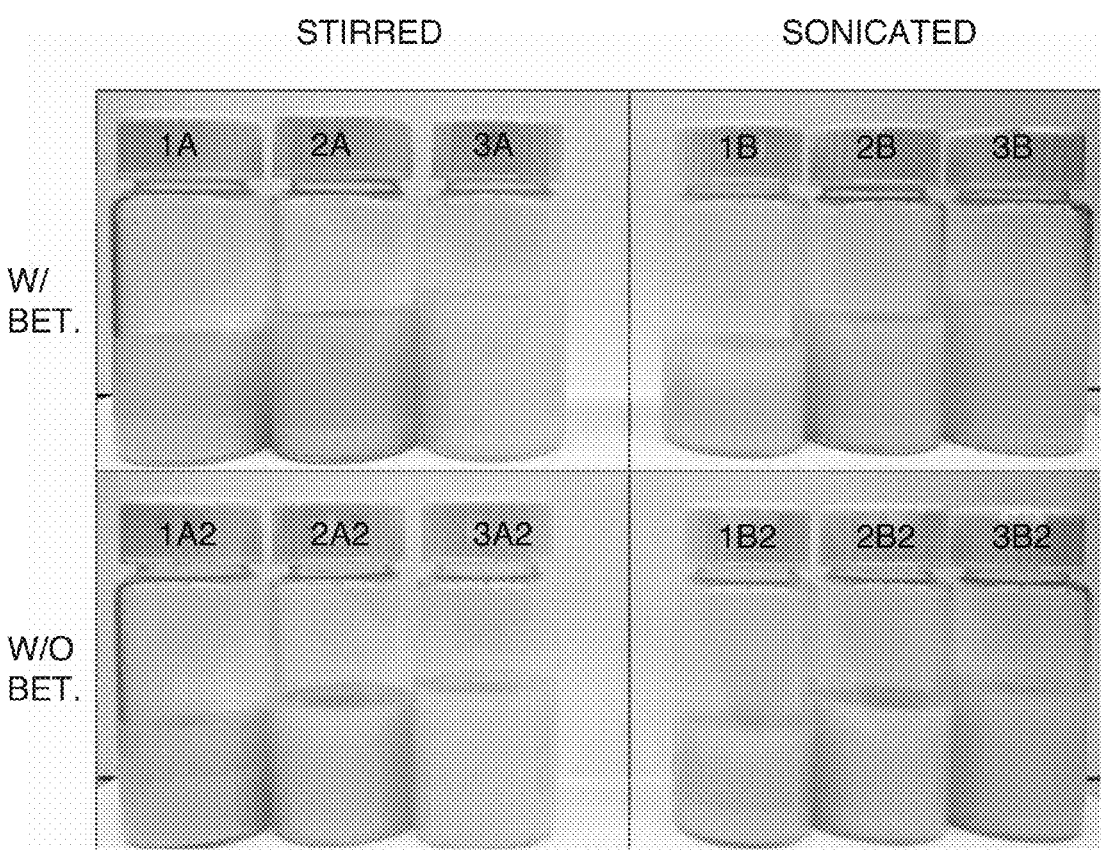
FIG. 5. Shown is the effect of sonication on stability of the wetness-indicating ink of the present invention.

FIG. 5 shows the results of sonification. In both the first row (with betaine) and second row (without betaine), it can be seen that sonication helps to stabilize the solution for a 24 hour period.

Changing Order of Addition of Each Ink Component. Two solutions were made: one containing dye (30 mg), developer (180 mg), and surfactant (2 g) and the other solution containing water (2.0 g), Hydroxypropyl-modified guar gum (JAGUAR HP 60 (4.0 g)), and binder (2.5 g). Each solution was stirred for 3 minutes and vortexed aggressively for 30 seconds, then the surfactant-containing portion was added to the stabilizer-containing mixture and the combined solution was stirred/vortexed.

Preparing the solution separately in two parts, A and B, and then subsequently combining the two parts was found to 1) be a more efficient method of mixing, and 2) increase the stability of the formulation over a 48-hour period. When this ink was disposed onto filter paper, allowed to dry, and insulted with water, the color response was vibrant.

Water-Indicating Ink Formulation (Weight %):
0.3% Leuco dye (Crystal Violet Lactone)
1.7% developer (4,4'-dihydroxybenzophenone)
6.0% desensitizer (betaine (1 g/mL solution concentration))
10.0% surfactant mixture (3:1 weight % mixture of PEG-8 Laurate:Polysorbate-80)
20.0% binder (AQUAKING Vehicle—Sun Chemical)
62.0% water+stabilizer (0.75 weight % JAGUAR HP-60—Rhodia Novecare)

The wetness-indicating ink formulation is prepared from the above-noted components as follows: combine 0.030 g dye and 0.170 g developer with 1.0 g surfactant mixture with light heating and heavy stirring to promote complexation. Once a color of relatively high intensity is seen, 600 µL of betaine solution is added, which causes the color to disappear. Next, an appropriate amount of water is added to the vial with constant stirring. An effective amount of stabilizer is then added and the solution mixed completely. Finally, 2.10 mL of binder is added to the resulting mixture. The solution is then stirred for about 5 minutes.

To prepare test samples, a discrete amount of the mixture is pipetted onto a substrate, and allowed to dry completely. Once dry, a small amount of water is pipetted onto the dried ink area of the substrate. Upon wetting, a color of relative intensity appears to the unaided eye.

The present invention has been described both generally and in detail by of example. Persons skilled in the art, however, can appreciate that the invention is not limited necessarily to the embodiments specifically disclosed, but that substitutions, modifications, and variations may be made to the present invention and its uses without departing from the spirit and scope of the invention. Therefore, changes should be construed as included herein unless the modifications otherwise depart from the scope of the present invention as defined in the following claims.

The invention claimed is:

1. A color-appearing ink composition comprising:
    a surfactant blend comprising a nonionic surfactant having a hydrophilic-lipophilic balance value greater than 10, and a surfactant selected from the group consisting of Polyethylene Glycol Ester of Lauric Acid, Ethoxylated Alkyl Phenol, Polyoxyethylene Sorbitan Monooleate, Disodium Lauryl Phenyl Ether Disulfonate, and any combination thereof;
    a water-insoluble leuco dye;
    a developer;
    a desensitizer comprising betaine or a betaine derivative;
    a binder;
    a stabilizer; and
    water
    wherein the composition is substantially free of organic solvent; and
    wherein the composition develops color from a substantially non-colored state when contacted by an aqueous liquid.

2. The color-appearing ink composition of claim 1 wherein the developer is 4,4'-dihydroxybenzophenone.

3. The color-appearing ink composition of claim 1 wherein the desensitizer is a betaine derivative having an average molecular weight of 100 to 800.

4. The color-appearing ink composition of claim 1 wherein the binder is selected from the group consisting of water-based emulsions of water-insoluble polymers binders, cellulose derivatives, polyamides and their copolymers, polyesters and their copolymers, phenolic resins, and polyanhydrides.

5. The color-appearing ink composition of claim 1 wherein stabilizer is hydroxypropyl-modified guar gum.

6. The color-appearing ink composition of claim 1, wherein the desensitizer comprising betaine or a betaine derivative is selected from the group consisting of: betaine, sodium bis-hydroxyethylglycinate lauryl-glucosides crosspolymer, sodium bis-hydroxyethylglycinate coco-glucosides crosspolymer, betaine ester-menthol, and betaine hydrocholoride.

* * * * *